United States Patent [19]

Baker et al.

[11] Patent Number: 6,001,781
[45] Date of Patent: Dec. 14, 1999

[54] PROCESS FOR PREPARING CONDENSATION PRODUCT OF HYDROXY-SUBSTITUTED AROMATIC COMPOUNDS AND GLYOXYLIC REACTANTS

[75] Inventors: Mark R. Baker, Lyndhurst; Karen M. Hull, Willoughby; David L. Westfall, Lakewood, all of Ohio

[73] Assignee: The Lubrizol Corporation, Wickliffe, Ohio

[21] Appl. No.: 08/927,504

[22] Filed: Sep. 10, 1997

[51] Int. Cl.⁶ .................... C10M 129/54; C07D 307/00; C07C 231/02

[52] U.S. Cl. .................... 508/305; 508/222; 508/553; 508/554; 549/295; 549/299; 549/326; 564/134

[58] Field of Search .................... 508/305; 549/326

[56] References Cited

U.S. PATENT DOCUMENTS

| | | | |
|---|---|---|---|
| 3,966,807 | 6/1976 | Elliott et al. | 508/555 |
| 4,051,049 | 9/1977 | Elliott et al. | 508/554 |
| 5,281,346 | 1/1994 | Adams et al. | 252/38 |
| 5,336,278 | 8/1994 | Adams et al. | 44/419 |
| 5,356,546 | 10/1994 | Blystone et al. | 252/35 |
| 5,441,653 | 8/1995 | Cleveland et al. | 508/270 |
| 5,458,793 | 10/1995 | Adams et al. | 252/47 |
| 5,560,755 | 10/1996 | Adams et al. | 44/341 |
| 5,620,949 | 4/1997 | Baker et al. | 508/452 |
| 5,629,448 | 5/1997 | Lange et al. | 564/134 |
| 5,686,625 | 11/1997 | Kos | 548/457 |

FOREIGN PATENT DOCUMENTS

| | | | |
|---|---|---|---|
| 799355A2 | 6/1997 | European Pat. Off. | C10M 129/44 |

*Primary Examiner*—Ellen M. McAvoy
*Attorney, Agent, or Firm*—David M. Shold; Beverly Pawlikowski

[57] ABSTRACT

The present invention is directed to a process for preparing a condensation product of a glyoxylic reactant and a hydrocarbyl-substituted aromatic compound having at least one hydroxy functionality, which includes (a) providing the glyoxylic reactant in the form of a compound represented by the formula

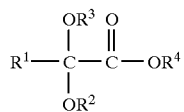

or its reactive equivalent, wherein $R^1$ and $R^3$ independently are hydrogen or hydrocarbyl group of 1 to about 4 carbon atoms; and $R^2$ and $R^4$ independently are hydrocarbyl groups of 1 to about 4 carbon atoms; (b) mixing the aromatic compound with the glyoxylic reactant; and (c) heating the mixture to a temperature of about 50° C. to about 200° C. in the presence of an acid catalyst for a sufficient time to form the condensation product.

33 Claims, No Drawings

PROCESS FOR PREPARING CONDENSATION PRODUCT OF HYDROXY-SUBSTITUTED AROMATIC COMPOUNDS AND GLYOXYLIC REACTANTS

BACKGROUND OF THE INVENTION

The present invention relates to a process for preparing compositions useful as fuel and lubricant additives. More specifically, the process involves the condensation of a glyoxylic reactant with a hydrocarbyl substituted aromatic compound having at least one hydroxy functionality.

U.S. Pat. No. 5,281,346, Adams et al., Jan. 25, 1994 discloses a lubricant additive for two-cycle engines, said additive comprising at least one compound of the general formula

  (I)

wherein M represents one or more metal ions, y is the total valence of all M and A represents one or more anion counting groups having a total of about Y individual anionic moieties and each anion containing group is a group of the formula

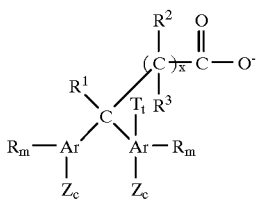

wherein T is selected from the group consisting of

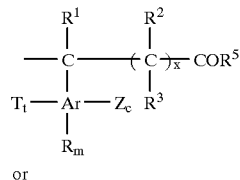

or

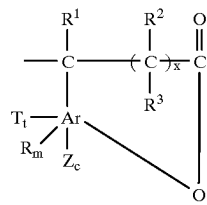

The products of formula (I) have been disclosed to be readily prepared by use of a carboxylic reactant, an embodiment of which was glyoxylic acid, represented in its hydrated form as

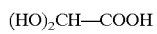

U.S. Pat. No. 5,458,793, Oct. 17, 1995 discloses a process comprising first forming an intermediate by reacting at an elevated temperature (a) at least one reactant of the formula

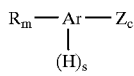

with
(b) a carboxylic reactant of the formula

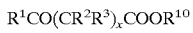

and then reacting the intermediate so formed at a temperature ranging from about 100° C. to about 250° C. with an amine of the formula

Glyoxylic acid is the preferred embodiment of the carboxylic reactant.

U.S. Pat. No. 5,560,755, (Adams et al., Oct. 1, 1996), 5,336,278 (Adams et al., Aug. 9, 1994) and 5,356,546 (Blystone et al., Oct. 18, 1994) disclose intermediates for fuel compositions prepared by reacting polybutene-substituted phenol and gloxylic acid in the presence of para-toluene sulfonic acid.

European Patent Application, EP 0779,355 A2, Kocsis et al., Jun. 18, 1997 discloses that lubricants which comprise, as an additive a salt of the reaction product of (i) glyoxylic acid or a hydrocarbyl substituted glyoxylic acid and (ii) a hydroxyaromatic compound, at least a portion of the molecules of which are alkylsubstituted, are useful for lubricating ceramic-containing engines, high temperature engines, and natural gas-fueled engines. Reactive equivalents of glyoxylic acid are disclosed to be acetals, half-acetals, esters, and the like.

SUMMARY OF THE INVENTION

The present invention is directed toward a process for preparing a condensation product of a glyoxylic reactant and a hydrocarbyl-substituted aromatic compound having at least one hydroxy functionality, comprising the steps of:

(I) providing the glyoxylic reactant in the form of a compound represented by the formula

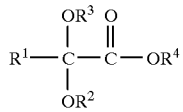

or a reactive equivalent thereof, wherein $R^1$ and $R^3$ independently are hydrogen or hydrocarbyl group of 1 to about 4 carbon atoms; and $R^2$ and $R^4$ independently are hydrocarbyl groups of 1 to about 4 carbon atoms;

(II) mixing the aromatic compound with the glyoxylic reactant; and (III) heating the mixture to a temperature of about 50° C. to about 200° C. in the presence of an acid catalyst for a sufficient time to form said condensation product.

DETAILED DESCRIPTION OF THE INVENTION

The process of this invention involves reacting a hydrocarbyl-substituted aromatic compound having at least one hydroxy functionality with a glyoxylic reactant.

The aromatic compound can include a single aromatic nucleus, such as a benzene nucleus, a pyridine nucleus, a thiophene nucleus, a 1,2,3,4-tetrahydronaphthalene nucleus, etc., or a polynuclear aromatic moiety. Such polynuclear moieties can be of the fused type, that is wherein at least two aromatic nuclei are fused at two points to another nucleus such as found in naphthalene and anthracene, or of the linked type wherein wherein at least two nuclei (either mono- or polynuclear) are linked through bridging linkages (such as carbon—carbon single bonds, ether linkages and carbonyl group containing linkages) to each other. Detailed examples of fused and linked structures can be found in U.S. Pat. Nos. 5,281,346; 5,336,278; 5,356,546; and 5,458,793. The preferred aromatic compound of this invention is a hydrocarbylphenol represented by the formula

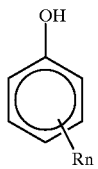

wherein n is 1 or 2; and R is a hydrocarbyl group of 4 to 500 carbon atoms; more preferably 4 to 120 carbon atoms; and most preferably 16 to 100 carbon atoms. The hydrocarbyl group(s) R attached to the aromatic ring is derived from any natural or synthetic aliphatic hydrocarbon. Thus, this material can be obtained from mineral oils or other natural hydrocarbons or organic materials. It can also be prepared synthetically. For example, polymers, copolymers or the corresponding hydrogenated polymers or copolymers obtained from the polymerization of olefinic hydrocarbons, such as $C_2$ to $C_6$ olefins, having the prescribed molecular weight are useful. Ethylene, propylene, 1,2-butylene, isobutylene and 2,3-butylene are particularly useful for preparing a suitable aliphatic hydrocarbon. The R group attached to the substituted phenol will generally be saturated; however a small amount (typically less than 5 mole %) of olefinic unsaturation can be present without undesirable effects. A preferred source of the group R is poly(isobutene)s obtained by polymerization of a $C_4$ refinery stream having a butene content of 35 to 75 weight percent and isobutene content of 30 to 60 weight percent, in the presence of a Lewis acid catalyst such as aluminum trichloride or boron trifluoride. These polybutenes typically contain predominantly (greater than 80% of total repeating units) isobutene repeating units of the configuration

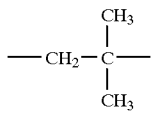

These polybutenes are typically monoolefinic, that is, they contain but one olefinic group per molecule said olefinic group being present as an end group.

In one embodiment, the monoolefinic end groups are vinylidene groups, i.e., groups of the formula

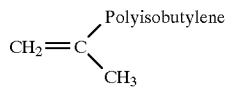

although the polybutenes may also comprise other olefinic configurations.

In one embodiment, the polybutene comprises about at least 50%, more preferably at least 60% vinylidene end groups. Such materials and methods for preparing them are described in U.S. Pat. Nos. 5,286,823 and 5,408,018. They are commercially available for example under the tradenames Ultravis™ (BP Chemicals) and Glissopal™ (BASF). In these cases where R is a polyisobutenyl group derived from a polymer of isobutene, said polymer having at least 60% of vinylidene end groups, R preferably has a number average molecular weight of 500 to 2000, more preferably 600 to 1300.

Numerous methods are known for preparing the hydrocarbyl substituted phenols described above and any of these are considered suitable for preparing the hydrocarbyl substituted aromatic compound of this invention. Techniques for alkylating phenols are well known to those skilled in the art. See, for example, the discussion in the article entitled "Alkylation of Phenols" in Kirk-Othmer "Encyclopedia of Chemical Technology", Second Edition, Vol. 1, pages 894–895, Interscience Publishers, a division of John Wiley and company, N.Y., 1963. One particularly suitable technique is the Friedel-crafts reaction, wherein an olefin (e.g., a polymer containing an olefinic bond, or halogenated or hydrohalogenated analog thereof), is reacted with a phenol. The reaction occurs in the presence of a Lewis acid catalyst (e.g., boron trifluoride and its complexes with ethers, phenols, hydrogen fluoride, etc., aluminum chloride, aluminum bromide, zinc dichloride, etc.). Other equally appropriate and convenient techniques for attaching the hydrocarbyl group R to the aromatic ring will occur readily to those skilled in the art.

The glyoxylic reactant of this invention can be represented by the formula

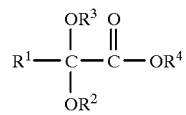

or a reactive equivalent thereof, wherein $R^1$ and $R^3$ independently are hydrogen or hydrocarbyl group of 1 to about 4 carbon atoms; and $R^2$ and $R^4$ independently are hydrocarbyl groups of 1 to about 4 carbon atoms. Preferably $R^3$ is hydrogen.

In a preferred embodiment, both $R^1$ and $R^3$ are hydrogen and both $R^2$ and $R^4$ are methyl; in otherwords, in this preferred embodiment, the glyoxylic reactant is represented by the structure

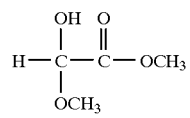

and known as glyoxylic acid methylester methylhemiacetal ("GMHA"). It is marketed by DSM Fine Chemicals.

The phrase "reactive equivalent" of a material, means any compound or chemical composition other than the material itself which reacts like the material itself under the reaction conditions. For example, reactive equivalents of formaldehyde include paraformaldehyde and formalin (an aqueous solution of formaldehyde). Reactive equivalents of the glyoxylic reactant can include 1,3,5-trioxane compounds represented by the structure

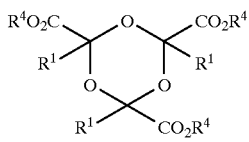

wherein $R^1$ and $R^4$ are defined as above. In a preferred embodiment $R^1$ is hydrogen and $R^4$ is methyl.

Although glyoxylic acid, represented in its hydrate form as $(HO)_2CH\text{---}COOH$, might be considered to be a reactive equivalent of GMHA, since it can also react with the hydrocarbyl substituted aromatic compound of this invention to give condensation products similar to reacting GMHA and the hydrocarbyl substituted aromatic compound, for purposes of this invention, glyoxylic acid is not considered to be a reactive equivalent of GMHA, because of several unique advantages of GMHA over glyoxylic acid (as will be discussed shortly).

In terms of manufacture, GMHA is a precursor to glyoxylic acid in a commercial process to make glyoxylic acid as shown below:

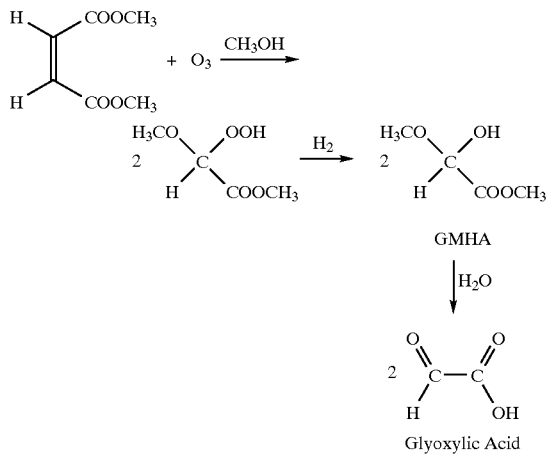

The process of the present invention involves mixing the aromatic compound with the glyoxylic reactant, and further heating the mixture to a temperature of 50° C. to 200° C. in the presence of an acid catalyst for a sufficient time to form a condensation product.

Mixing of the Reactants

The glyoxylic reactant can be mixed with the aromatic compound all at once as in a batch reaction or can be added dropwise or metered into a reactor over a period of time. Compared to glyoxylic acid, GMHA is more miscible with the aromatic compound (which is considerably more nonpolar or has substantially greater hydrocarbon character than either GMHA or glyoxylic acid), owing to the lower polarity of an ester such as GMHA compared to a carboxylic acid such as glyoxylic acid. Furthermore, the absence of water in GMHA makes mixing of GMHA and the aromatic compound easier than mixing of glyoxylic acid and the aromatic compound. However, it is still important to insure good mixing of GMHA and the aromatic compound. In large scale synthesis (about 400–40,000 liters), the reaction mixture is mixed employing a mixing energy of at least 1.48 watts/liter (7.5 horsepower/1000 gallons) In terms of the type of dispersion in the reactor, impellers that impart an axial dispersion pattern have been shown to provide improved GMHA conversion as compared to those impellers that impart a radial dispersion pattern. The reaction may be conducted in or without the presence of a suitable inert solvent.

Reaction Temperature

Although the process can be carried out at any temperature in the range of 50° C. to 200° C., the preferred reaction temperature for the process is 100–150° C., due to the relative absence of foaming and the ease of vacuum stripping within this temperature range.

The Acid Catalyst

The process is carried out in the presence of an acid catalyst which can include a sulfonic acid or a mineral acid. Particularly illustrative catalysts of the first type are illustrated by methanesulfonic acid and para-toluenesulfonic acid catalysts. Illustrative examples of a mineral acid include hydrochlooric acid, sulfuric acid and nitric acid. The preferred acid catalyst of the present invention is methanesulfonic acid.

The acid catalyst is generally present at a level of 1 to 10 mole %, preferably at a level of 2 to 5 mole % with respect to the glyoxylic reactant.

Mole Ratio of Reactants

Normally the mole ratio of the hydrocarbyl-substituted aromatic compound to the glyoxylic reactant will be 5:1 to 1:2, preferably 1.8:1 to 2.2:1, and more preferably about 2:1; however, useful products may be obtained by employing an excess amount of either reactant. Thus molar ratios of the hydrcarbyl-substituted aromatic compound to the glyoxylic reactant of 1:1, 2:1, 1:2, 3:1, etc. are contemplated and useful products may be obtained thereof.

The Condensation Product

The product of this process involving the reaction of the hydroxy containing hydrocarbyl-substituted aromatic compound and glyoxylic reactant may be an ester, a carboxylic acid or a lactone or mixtures thereof. In particular, when the hydroxy aromatic reactant is such that the position of substituents on the hydroxy aromatic reactant hinder the formation of a lactone, the product from the hydroxy aromatic compound and the glyoxylic reactant will essentially comprise an ester or a carboxylic acid or mixtures thereof. For example when the hydroxy aromatic compound is 2,6-dihydrocarbylphenol, the product mixture will essentially consist only of a carboxylic acid, ester, or mixtures thereof. On the other hand, when the position of the substituents on the hydroxy aromatic reactant are such that lactone formation is not substantially hindered, the product comprises mostly a lactone. For example, with 2,4-dihydrocarbylphenol, the product is mostly a lactone with no more than 5–15% of carboxylic acid, ester, or mixtures thereof.

Thus, when the aromatic compound is a hydrocarbyl-substituted (mono or di-substituted) phenol represented by the formula

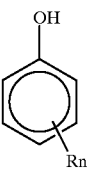

wherein the R group(s) are not in a position to hinder the formation of a lactone, the condensation product normally comprises a lactone of the formula

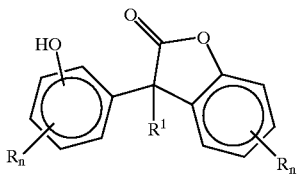

wherein R is a hydrocarbyl group of 4 to 500 carbon atoms; $R^1$ is defined as above; and each n independently is 1 or 2. When the glyoxylic reactant is GMHA, $R^1$ is hydrogen.

This type of coupled lactone structure is normally generated by the condensation of 2 moles of the aromatic compound and 1 mole of the glyoxylic reactant. Using hydrocarbyl phenol and GMHA as illustrative examples of reactants, the reaction can be represented by the following equation.

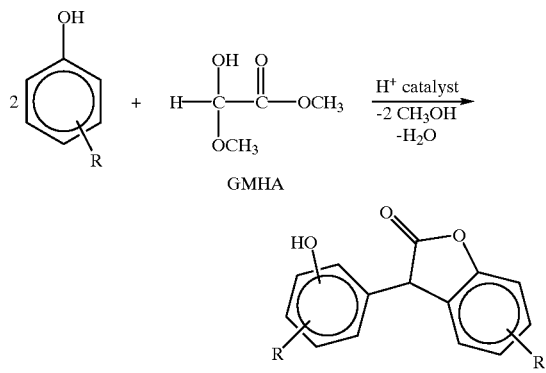

wherein R is a hydrocarbyl group. However compositions containing more than one lactone structure (i.e. overcoupled composition) may also be present, especially in a process employing a reaction mixture more enriched in the glyoxylic reactant than a 2:1 molar ratio of the aromatic compound and glyoxylic reactant, i.e. less than a 2:1 molar ratio of the aromatic compound and the glyoxylic reactant. An illustrative example of an overcoupled lactone composition containing multiple lactone functionalities may be represented by the formulae

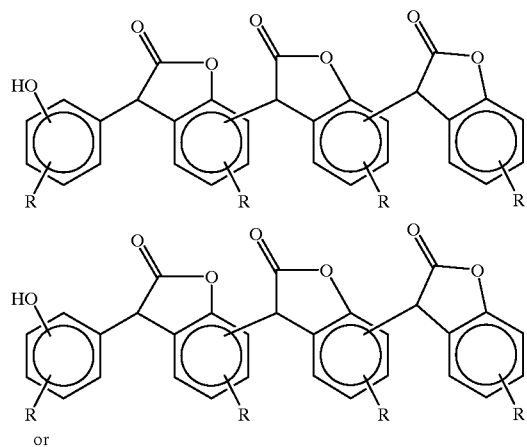

or

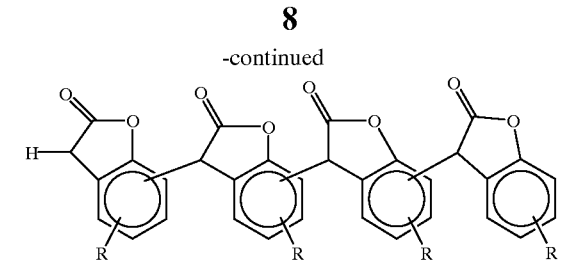

wherein R is a hydrocarbyl group and where GMHA is used illustratively as the glyoxylic reactant.

As already mentioned, for the purposes of this invention, acids represented by the formula RC(O)COOH or represented in their hydrated form as $RC(OH)_2COOH$ are not to be considered reactive equivalents of the glyoxylic reactants of this invention. These acids and their reactions with hydroxy-substituted aromatic compounds have been disclosed in U.S. Pat. Nos. 5,281,346; 5,336,278; 5,356,546; and 5,458,793. Thus glyoxylic acid, for the purposes of this invention is not a reactive equivalent of GMHA. Furthermore, GMHA has several advantages over the use of glyoxylic acid. One of these is the higher conversion of the phenolic lactone products with GMHA. This may in part be due to increased contact (due to greater miscibility) between GMHA and some starting hydrocarbylphenols. This has especially been found for phenols where the hydrocarbyl group is polybutenyl group, including polybutenyl group having an olefin end group where at least 60% of the olefin end group are of vinylidene structure. This results in improved conversion to the phenolic lactone products, without the need for capital to implement complex and more efficient stirring mechanisms in a production scale manufacturing process.

In addition, use of GMHA in place of glyoxylic acid results in a composition that has considerably lower (about 20–30% lower) amount of overcoupled lactone side products, especially in scale-up synthesis using the process of this invention. Some illustrative structures of overcoupled lactone structures have been given and discussed above.

Another highly favored aspect of GMHA over glyoxylic acid is its negligible corrosivity toward stainless steel reactors.

The condensation product prepared by the process of this invention can be further reacted with amines, reactive metals or metal compounds to give additional useful compositions. Suitable amine reactants and reactive metals and metal compounds will be described hereinbelow.

Amine Reactant

Suitable amine reactants include ammonia and other amines as described hereinbelow, and mixtures thereof.

One type of amines include monoamines. The monoamines generally contain from 1 to 24 carbon atoms, preferably 1 to 12, and more preferably 1 to 6. Examples of monoamines useful in the present invention include hydrocarbylamines which may be primary, secondary or tertiary. Examples of primary amines include methylamine, ethylamine, propylamine, butylamine, octylamine, and dodecylamine. Examples of secondary amines include dimethylamine, diethylamine, dipropylamine, dibutylamine, methylbutylamine, and ethylhexylamine. Tertiary monoamines will only form salts, for example, with carboxylic acid groups.

The monoamine may also be a hydroxyamine. Typically, the hydroxyamines are primary or secondary alkanolamines or mixtures thereof. As stated above, tertiary monoamines will only form salts; however tertiary alkanol monoamines sometimes can react to form an ester which contains a tertiary amino group. containing ester. Tertiary alkanolamines tend to resist reaction with the lactone intermediate (i.e. the lactone functionality present in the reaction product of the hydroxy containing aromatic compound and the glyoxylic reactant). However, when the intermediate contains carboxylic acid groups, reaction with the —OH group of alkanolamines can lead to ester formation. Alkanol amines that can react to form products other than salts can be represented, for example, by the formulae:

H$_2$N—R'—OH, and

R$^4$HN—R'—OH, wherein each R$^4$ is independently a hydrocarbyl group of one to 22 carbon atoms or hydroxyhydrocarbyl group of 2 to 22 carbon atoms, preferably 1 to 4, and R' is a divalent hydrocarbyl group of 2 to about 18 carbon atoms, preferably 2 to 4. The group —R'—OH in such formulae represents the hydroxyhydrocarbyl group. R' can be an acyclic, alicyclic or aromatic group. Typically, R' is an acyclic straight or branched alkylene group such as an ethylene, 1,2-propylene, 1,2-butylene, 1,2-octadecylene, etc. group. When two R$^4$ groups are present in the same molecule they can be joined by a direct carbon-to-carbon bond or through a heteroatom (e.g., oxygen, nitrogen or sulfur) to form a 5-, 6-, 7- or 8-membered ring structure. Examples of such heterocyclic amines include N-(hydroxyl lower alkyl)-morpholines, -thiomorpholines, -piperidines, -oxazolidines, -thiazolidines and the like. Typically, however, each R$^4$ is independently a methyl, ethyl, propyl, butyl, pentyl or hexyl group.

Examples of these alkanolamines include di- and triethanolamine, diethylethanolamine, ethylethanolamine, and butyldiethanolamine.

The hydroxyamines can also be ether group containing N-(hydroxyhydrocarbyl) amines. These are hydroxypoly (hydrocarbyloxy) analogs of the above-described hydroxy amines (these analogs also include hydroxyl-substituted oxyalkylene analogs). Such N-(hydroxyhydrocarbyl) amines can be conveniently prepared, for example, by reaction of epoxides with aforedescribed amines and can be represented by the formulae:

H$_2$N—(R'O)$_x$—H,

R$^4$HN—(R'O)$_x$—H, and

R$^4$HN—(R'O)$_x$—H wherein x is a number from 2 to 15 and R$^4$ and R' are as described above. R$^4$ may also be a hydroxypoly (hydrocarbyloxy) group.

The amine may also be a polyamine. The polyamine may be aliphatic, cycloaliphatic, heterocyclic or aromatic. Examples of the polyamines include alkylene polyamines, hydroxy containing polyamines, arylpolyamines, and heterocyclic polyamines.

Other useful amines include ether amines of the general formula

R$^6$OR$^1$NHR$^7$ wherein R$^6$ is a hydrocarbyl group, preferably an aliphatic group, more preferably an alkyl group, containing from 1 to 24 carbon atoms, R$^1$ is a divalent hydrocarbyl group, preferably an alkylene group, containing from 2 to 18 carbon atoms, more preferably 2 to 4 carbon atoms and R$^7$ is H or hydrocarbyl, preferably H or aliphatic, more preferably H or alkyl, more preferably H. When R$^7$ is not H, then it preferably is alkyl containing from 1 to 24 carbon atoms.

Alkylene polyamines are represented by the formula

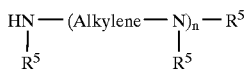

wherein n has an average value between 1 and 10, preferably 2 to 7, more preferably 2 to 5, and the "Alkylene" group has from 1 to 10 carbon atoms, preferably 2 to 6, more preferably 2 to 4. R$^5$ is independently hydrogen, aliphatic, hydroxy- or amine-substituted aliphatic group of up to about 30 carbon atoms. Preferably R$^5$ is H or lower alkyl, most preferably, H. An example of a polyamine having a terminal dialkylamino group is 3-dimethylaminopropylamine.

Alkylene polyamines include methylene polyamines, ethylene polyamines, butylene polyamines, propylene polyamines, pentylene polyamines, etc. Higher homologues and related heterocyclic amines such as piperazines and N-amino alkyl-substituted piperazines are also included. Specific examples of such polyamines are tris-(2-aminoethyl)amine, propylene diamine, trimethylene diamine, tripropylene tetramine, etc.

Higher homologues obtained by condensing two or more of the above-noted alkylene amines are similarly useful as are mixtures of two or more of the aforedescribed polyamines.

Ethylene polyamines, such as some of those mentioned above, are preferred. They are described in detail under the heading Ethylene Amines in Kirk Othmer's "Encyclopedia of Chemical Technology", 2d Edition, Vol. 7, pages 22–37, Interscience Publishers, New York (1965). Such polyamines are most conveniently prepared by the reaction of ethylene dichloride with ammonia or by reaction of an ethylene imine with a ring opening reagent such as water, ammonia, etc. These reactions result in the production of a complex mixture of polyalkylene polyamines including cyclic condensation products such as the aforedescribed piperazines.

In one embodiment, the ethylene polyamine is diethylene triamine (DETA).

Other useful types of polyamine mixtures are those resulting from stripping of the above-described polyamine mixtures to leave as residue what is often termed "polyamine bottoms". In general, alkylene polyamine bottoms can be characterized as having less than two, usually less than 1% (by weight) material boiling below about 200° C. A typical sample of such ethylene polyamine bottoms obtained from the Dow Chemical Company of Freeport, Tex., designated "E-100" has a specific gravity at 15.6° C. of 1.0168, a percent nitrogen by weight of 33.15 and a viscosity at 40° C. of 1.21×10$^{-4}$ m$^2$/s (121 centistokes). Gas chromatography analysis of such a sample contains about 0.93% "Light Ends" (most probably diethylenetriamine), 0.72% triethylenetetramine, 21.74% tetraethylene pentaamine and 76.61% pentaethylene hexamine and higher (by weight). These alkylene polyamine bottoms include cyclic condensation products such as piperazine and higher analogs of diethylenetriamine, triethylenetetramine and the like.

Another useful polyamine is a condensation product obtained by reaction of at least one hydroxy compound with at least one polyamine reactant containing at least one primary or secondary amino group. The hydroxy compounds are preferably polyhydric alcohols and amines. Preferably the hydroxy compounds are polyhydric amines. Polyhydric amines include any of the above-described monoamines reacted with an alkylene oxide (e.g., ethylene oxide, propylene oxide, butylene oxide) having 2 to 20 carbon atoms, preferably 2 to 4. Examples of polyhydric amines include tri-(hydroxypropyl)amine, tris-(hydroxymethyl)amino methane, 2-amino-2-methyl-1,3-propanediol, N,N,N',N'-tetrakis (2-hydroxypropyl) ethylenediamine, and N,N,N',N'-tetrakis (2-hydroxyethyl) ethylenediamine.

Polyamine reactants, which react with the polyhydric alcohol or amine to form the condensation products or condensed amines, are described above. Preferred polyamine reactants include triethylenetetramine (TETA), tetraethylenepentamine (TEPA), pentaethylenehexamine (PEHA), and mixtures of polyamines such as the above-described "amine bottoms".

The condensation reaction of the polyamine reactant with the hydroxy compound is conducted at an elevated temperature, usually 60° C. to 265° C. in the presence of an acid catalyst. The amine condensates and methods of making the same are described in Steckel (U.S. Pat. No. 5,053, 152).

The polyamines can include hydroxy-containing polyamines. Hydroxy-containing polyamine analogs of hydroxy monoamines, particularly alkoxylated alkylenepolyamines can also be used. Such polyamines can be made by reacting the above-described alkylene amines with one or more of the above-described alkylene oxides. Similar alkylene oxide-alkanolamine reaction products can also be used such as the products made by reacting the aforedescribed primary, secondary or tertiary alkanolamines with ethylene, propylene or higher epoxides in a 1.1 to 1.2 molar ratio. Reactant ratios and temperatures for carrying out such reactions are known to those skilled in the art.

Specific examples of alkoxylated alkylenepolyamines include N,N-di-(2-hydroxyethyl)-ethylenediamine and 1-(2-hydroxyethyl)piperazine. Higher homologues obtained by condensation of the above illustrated hydroxy-containing polyamines through amino groups or through hydroxy groups are likewise useful. Condensation through amino groups results in a higher amine accompanied by removal of ammonia while condensation through the hydroxy groups results in products containing ether linkages accompanied by removal of water. Mixtures of two or more of any of the aforesaid polyamines are also useful.

The polyamine may also be a heterocyclic polyamine. The heterocyclic polyamines include aziridines, azetidines, azolidines, tetra- and dihydropyridines, pyrroles, indoles, piperidines, imidazoles, di- and tetrahydroimidazoles, piperazines, isoindoles, purines, N-aminoalkylmorpholines, N-aminoalkylthiomorpholines, N-aminoalkylpiperazines, N,N'-bis-aminoalkylpiperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, or nitrogen with oxygen and/or sulfur in the hetero-atom containing ring, especially the piperidines, piperazines, thiomorpholines, morpholines, pyrrolidines, and the like. Usually the aminoalkyl substituents are substituted on a nitrogen atom forming part of the hetero ring. Specific examples of such heterocyclic amines include N-aminopropylmorpholine, N-aminoethylpiperazine, and N,N'-diaminoethylpiperazine. Hydroxy alkyl substituted heterocyclic polyamines are also useful. An example is N-hydroxyethylpiperazine.

The amine can also include a polyalkene-substituted amine. These polyalkene-substituted amines are well known to those skilled in the art. They are disclosed in U.S. Pat. Nos. 3,275,554; 3,438,757; 3,454,555; 3,565,804; 3,755,433; and 3,822,289.

Typically, polyalkene-substituted amines are prepared by reacting halogenated-, preferably chlorinated-, olefins and olefin polymers (polyalkenes) with amines (mono- or polyamines). The amines may be any of the amines described above. Examples of these compounds include poly(propylene)amine; N,N-dimethyl-N-poly(ethylene/propylene)amine, (50:50 mole ratio of monomers); polybutene amine; N,N-di(hydroxyethyl)-N-polybutene amine; N-(2-hydroxypropyl)-N-polybutene amine; N-polybuteneaniline; N-polybutenemorpholine; N-poly(butene) ethylenediamine; N-poly(propylene)trimethylenediamine; N-poly(butene)diethylenetriamine; N',N'-poly(butene) tetraethylenepentamine; and N,N-dimethyl-N'-poly (propylene)-1,3-propylenediamine.

The polyalkene substituted amine is characterized as containing from at least 8 carbon atoms, preferably at least 30, more preferably at least 35 up to 300 carbon atoms, preferably 200, more preferably 100. In one embodiment, the polyalkene substituted amine is characterized by an Mn (number average molecular weight) value of at least 500. Generally, the polyalkene substituted amine is characterized by an Mn value of 500 to 5000, preferably 800 to 2500. In another embodiment n varies between 500 to 1200 or 1300.

The polyalkenes from which the polyalkene substituted amines are derived include homopolymers and interpolymers of polymerizable olefin monomers of 2 to 16 carbon atoms; usually 2 to 6, preferably 2 to 4, more preferably 4. The olefins may be monoolefins such as ethylene, propylene, 1-butene, isobutene, and 1-octene; or a polyolefinic monomer, preferably diolefinic monomer, such 1,3-butadiene and isoprene. Preferably, the polymer is a homopolymer. An example of a preferred homopolymer is a polybutene, preferably a polybutene in which about 50% of the polymer is derived from isobutylene. The polyalkenes are prepared by conventional procedures.

Suitable amine reactants can also include amines represented by the general formula

H—X—(CRF$^f_2$CR$^f_2$)—NH$_2$ (II)

wherein each R$^f$ is independently H, alkoxy, or hydroxyalkyl, containing from 1 to 8, preferably from 1 to 4 carbon atoms, hydrocarbyl, including alicyclic, acyclic or aromatic groups, preferably alicyclic groups containing from 1 to 24 carbon atoms, N-alkoxyalkyl- or hydroxyalkyl-substituted aminohydrocarbyl; and X is selected from O, S or —NR$^a$ wherein R$^a$ is H, hydrocarbyl including alicyclic, acyclic or aromatic groups, preferably alkyl or alkenyl groups containing from 1 to 24 carbon atoms, preferably from 8 to 18 carbon atoms, and hydroxyhydrocarbyl or aminohydrocarbyl containing from 1 to 8, preferably 1 to 4 carbon atoms, preferably aliphatic carbon atoms.

Illustrative of suitable amine reactants of formula (II) include alkanolamines, mercaptoalkyleneamines and di- and polyamines. Specific examples of suitable amines of formula (II) include ethanolamine, 2-aminopropanol, 2-methyl-2-amino-propanol, tri(hydroxymethyl)aminomethane, 2-mercaptoethylamine, ethylene diamine, 1-amino-2-methylaminoethane, diethylenetriamine, triethylenetetraamine and analogous ethylene polyamines, including amine-bottoms and condensed amines such as those described hereinbelow, and alkoxylated ethylenepolyamines such as N-(2-hydroxyethyl)ethylenediamine.

The product of the reaction of an amine with the condensation product (formed by reaction of the hydroxy containing aromatic compound and the glyoxylic reactant) will usually result from the reaction of the amine with the lactone intermediate, opening the lactone ring or from direct reaction with an ester or carboxylic acid group present in the product of the hydroxy containing aromatic compound and the glyoxylic reactant of this invention. It is generally preferred to utilize sufficient amine reactant to convert substantially all of the ester, carboxylic acid, lactone, or mixtures thereof to product; however, conversion of at least 50%, more preferably 75% of lactone, ester, carboxylic acid or mixtures thereof to product is often acceptable. Preferably, at least 90%, more preferably 95–100% conversion of lactone, ester, carboxylic acid or mixtures thereof to product is effected.

The reaction of a polyamine with the condensation product of this invention (said condensation product formed by reaction of the hydroxy containing aromatic compound and the glyoxylic reactant) can be conducted in the presence of an alcohol solvent as disclosed in U.S. Pat. No. 5,629,448. Two types of alcohols may be used as the solvent. The first is an aliphatic alcohol containing between 2–10 carbon atoms, preferably 4–10 carbon atoms, and most preferably 6–10 carbon atoms. Examples of suitable alcohols include decanol, octanol, 2-ethylhexanol, hexanol, pentanol, butanol, propanol, 2-propanol, and ethanol. In one embodiment, the alcohol is 2-ethylhexanol.

The second type of alcohol is a polyether alcohol represented by the formula

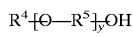

where $R^4$ is a hydrocarbyl group containing from 1 to 30 carbon atoms and $R^5$ is a 2 to 8, preferably 2 to 6, carbon alkylene group, and y is between 1 and 30. Non-limiting examples of suitable polyether alcohols include 2-butoxyethanol, 2-octyloxyethanol, 2-butoxypropanol, 2-(2-butoxy-propoxy)-ethanol, and 2-(lauryloxyethoxyethoxy)-ethanol. Either the polyether alcohol or the aliphatic alcohol may be used alone, or in combination with an inert, non-polar, solvent such as toluene or xylene.

The reaction of the lactone, ester, carboxylic acid or mixtures thereof with an amine to prepare the nitrogen-containing compounds is typically conducted at temperatures ranging from 25° C. to preferably 250° C. 50° C.–200° C., and more preferably 100–150° C. Amide, imidazoline, thiazoline or oxazoline formation may take place. Where imidazoline, oxazoline, or thiazoline formation takes place, it does so frequently by first forming the amide then continuing the reaction at elevated temperature (usually greater than 150° C.) to generate imidazoline, thiazoline or oxazoline by eliminating water. Infrared analysis during the reaction is a convenient means for determining the nature and extent of the reaction. The time required for conversion to the nitrogen-containing heterocyclic compound generally decreases with increased temperature.

The Reactive Metals and Metal Compounds

The reactive metals include but are not limited to alkali metals, alkaline earth metals, zinc, cadmium, lead, cobalt, nickel iron, manganese and copper. Preferred are the alkali and alkaline earth metals. Especially preferred are sodium, potassium, calcium, and lithium.

Examples of reactive metal compounds are sodium oxide, sodium hydroxide, sodium carbonate, sodium methylate, sodium phenoxide, corresponding potassium and lithium compounds, calcium oxide, calcium hydroxide, calcium carbonate, calcium methylate, calcium chloride, calcium phenoxide, and corresponding barium and magnesium compounds, zinc oxide, zinc hydroxide, zinc carbonae, cadmium chloride, lead oxide, lead hydroxide, lead carbonate, nickel oxide, nickel hydroxide, nickel nitrate, cobalt oxide, ferrous carbonate, ferrous oxide, cupric acetate, and cupric nitrate.

The above metal compounds are merely illustrative of those useful in this invention; however the invention is not considered as limited to such. Suitable metals and metal containing reactants are disclosed in many U.S. patents including U.S. Pat. Nos. 3,306,908; 3,271,310; and U.S. Pat. No. Re. 26,433.

The reaction product resulting from the reaction of the condensation product and the reactive metal or metal compound will preferably comprise a substantially neutral metal salt, which metal salt is a carboxylate and/or phenate. However, the salts may contain up to about 50% unreacted lactone, carboxylic acid, or ester group or mixtures thereof.

It is also to be understood that these salts may also be slightly basic, that is they may contain a small excess (up to about 10–15% excess) of metal beyond that which is normally expected based on the stoichiometry of the components. The excess metal is not used for the purpose of preparing overbased materials but for insuring that the reaction leading to salt formation is driven to completion.

As used herein, the term "hydrocarbyl substituent" or "hydrocarbyl group" is used in its ordinary sense, which is well-known to those skilled in the art. Specifically, it refers to a group having a carbon atom directly attached to the remainder of a molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a pre-dominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

EXAMPLES

Example 1

To a reactor equipped with a stirrer, thermowell, subsurface gas inlet tube (with nitrogen flowing at 8.5 L/hr (0.3 std. ft³/hr.) and a Dean Stark trap with a reflux condenser are charged 1227 grams (1.48 moles) of a polybutene substituted phenol (prewarmed to 60° C.) prepared by $BF_3$ catalyzed alkylation of phenol with a polybutene having a number average molecular weight of approximately 1000 and containing 2.04 weight % OH. GMHA (89.0 grams;

0.74 mole; Source: Chemie Linz), methanesulfonic acid (70% aqueous solution; 3.4 grams, 0.024 mole) and 0.5 gram of a kerosene solution of Dow Corning 200 Fluid viscosity $1\times10^{-3}$ m$^2$/s (1000 cSt) @ 25° C.) are charged to the reactor. The mixture is heated to 120° C. over 0.5 hour and stirring is begun. The reaction is held an additional 4 hours while collecting water and methanol in the Dean-Stark trap. After this time, 55 grams of distillate is collected. The reaction is vacuum stripped up to 1.07 kPa (8 mm Hg) at 120° C. for two hours or until distillation is complete. The total amount of distillate recovered during the lactonization is 58 grams. The residue (1235 grams) is the reaction product. The product is analyzed to contain mostly lactone functionality. Analysis: Saponification number (ASTM D94) is 32.7; IR 1788cm$^{-1}$; Acid number by titration: 32.4; unreacted phenolic starting material (by 13C NMR): 7 mole %.

Comparative Example 1

To a reactor equipped with a stirrer, thermowell, subsurface gas inlet tube (with nitrogen flowing at 8.5 L/hr (0.3 std. ft$^3$/hr.) and a Dean Stark trap with a reflux condenser are charged 1100 grams (0.95 mole) of a polybutene substituted phenol (prewarmed to 120° C.) prepared by BF$_3$ catalyzed alkylation of phenol with a polybutene having a number average molecular weight of approximately 1000 and containing 1.46 weight % OH. Glyoxylic acid (50 wt % in water; 70.0 grams; 0.47 mole), methanesulfonic acid (70 wt % aqueous solution; 1.5 grams, 0.011 mole) and 0.5 gram of a kerosene solution of Dow Corning 200 Fluid (viscosity $1\times10^{-3}$ m$^2$/s (1000 cSt) @ 25° C.) are charged to the reactor. The mixture is heated to 120° C. and maintained at that temperature for four (4) hours while collecting water and methanol in the Dean-Stark trap. The reaction is vacuum stripped up to 1.07 kPa (8 mm Hg) at 125° C. for two hours or until distillation is complete. The total amount of distillate recovered during the lactonization is 49.6 grams. The residue (1000 grams) is the reaction product. The product is analyzed to contain mostly lactone functionality. Analysis: Saponification number (ASTM D94) is 24.7; IR 1788cm$^{-1}$; Unreacted phenolic starting material (by $^{13}$C NMR): 21 mole %.

Example 2

Preparation of a nitrogen containing material from the product of Example 1: The product of Example 1 is heated to a temperature of 100° C. and Pertrose A24/36 solvent (an aromatic hydrocarbon solvent containing a mixture of heavy aromatic petroleum naphtha and hydrosulfurized petroleum kerosine) is charged to the reactor with stirring. 3-Dimethylaminopropylamine (66.3 grams; 0.65 mole) is charged over five minutes, based on 1235 grams of lactone (product of Example 1) having a saponification number (ASTM D94) of 32.7. The reaction is held for 2 hours. The reaction mixture is filtered over 1% diatomaceous earth filter aid. The filtrate is the reaction product. Analysis: 1.03%N; Base Neutralization number: 22.3; IR, 1640 cm$^{-1}$; 0.2% free amine; Color (ASTM D1500): L5.0; Specific gravity @ 15.6° C.: 0.9597; Flash Point (ASTM D93): 115° C.; Viscosity @ 1000 and 40° C.: $1.90\times10^{-4}$ and $6.66\times10^{-3}$ m$^2$/s respectively (190 and 6657 cSt respectively); Molecular weight by GPC: Mn=841; Mw=1487.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. It is to be understood that the amount, range, and ratio limits set forth herein may be combined. As used herein, the expression "consisting essentially of" permits the inclusion of substances which do not materially affect the basic and novel characteristics of the composition under consideration.

What is claimed is:

1. A process for preparing a condensation product of a glyoxylic reactant and a hydrocarbyl-substituted aromatic compound having at least one hydroxy functionality, comprising the steps of:

(I) providing the glyoxylic reactant in the form of a compound represented by the formula

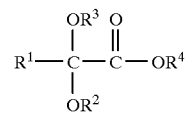

or a reactive equivalent thereof represented by the formula

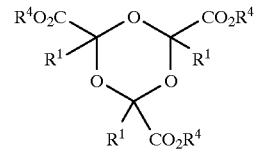

wherein in the above formulae R$^1$ and R$^3$ independently are hydrogen or hydrocarbyl group of 1 to about 4 carbon atoms; and R$^2$ and R$^4$ independently are hydrocarbyl groups of 1 to about 4 carbon atoms;

(II) mixing the aromatic compound with the glyoxylic reactant; and (III) heating the mixture to a temperature of about 50° C. to about 200° C. in the presence of an acid catalyst for a sufficient time to form said condensation product.

2. The process of claim 1 wherein R$^3$ is hydrogen.

3. The process of claim 2 wherein both R$^2$ and R$^4$ are methyl.

4. The process of claim 3 wherein R$^1$ is hydrogen.

5. The process of claim 1 wherein said aromatic compound is a phenol represented by the formula

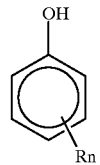

wherein n is 1 or 2; and R is a hydrocarbyl group of about 4 to about 500 carbon atoms.

6. The process of claim 1 wherein the condensation product comprises at least one lactone compound.

7. The process of claim 6 wherein said lactone compound is represented by the formula

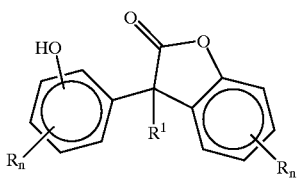

wherein R is a hydrocarbyl group of about 4 to about 500 carbon atoms; $R^1$ is defined as above; and each n independently is 1 or 2.

8. The process of claim 6 wherein $R^1$ is hydrogen.

9. The process of claim 5 wherein R is a hydrocarbyl group of about 4 to about 120 carbon atoms.

10. The process of claim 5 wherein R is a hydrocarbyl group of about 16 to about 100 carbon atoms.

11. The process of claim 5 wherein R is a polyisobutenyl group derived from a polymer of isobutene, said polymer having an olefin end group.

12. The process of claim 11 wherein at least 60% of the olefin end groups are of vinylidene structure.

13. The process of claim 11 wherein R has a number average molecular weight of about 500 to about 2000.

14. The process of claim 13 wherein the R has a number average molecular weight of about 600 to about 1300.

15. The process of claim 1 wherein the temperature is between about 100° C. to about 150° C.

16. The process of claim 1 wherein the acid catalyst is a sulfonic acid or a mineral acid.

17. The process of claim 16 wherein the acid catalyst is methanesulfonic acid.

18. The process of claim 1 wherein the acid catalyst is present at a level of about 1 to about 10 mole % of the glyoxylic reactant.

19. The process of claim 18 wherein the acid catalyst is present at a level of about 2 to about 5 mole % of the glyoxylic reactant.

20. The process of claim 1 wherein the mole ratio of the aromatic compound to the glyoxylic reactant is about 5:1 to about 1:2.

21. The process of claim 20 wherein the mole ratio of the aromatic compound to the glyoxylic reactant is about 1.8:1 to about 2.2:1.

22. The process of claim 1 wherein the aromatic compound and the glyoxylic reactant are mixed employing a mixing energy of at least 1.48 watts/liter.

23. The process of claim 1 further comprising reacting said condensation product with an amine.

24. The process of claim 23 wherein the amine is a polyamine.

25. The process of claim 24 wherein the polyamine is an alkylene polyamine.

26. The process of claim 25 wherein the alkylene polyamine is diethylene tetramine.

27. The process of claim 26 wherein said reaction of condensation product and diethylene tetramine is carried out in the presence of an alcohol solvent.

28. The process of claim 27 wherein said alcohol solvent is 2-ethylhexanol.

29. The process of claim 25 wherein the alkylene polyamine is 3-dimethylaminopropylamine.

30. The process of claim 1 further comprising reacting said condensation product with a reactive metal or a reactive metal compound.

31. The process of claim 30 wherein the reactive metal is selected from the group consisting of alkali metals and alkaline earth metals.

32. The process of claim 31 wherein the reactive metal is calcium.

33. A composition prepared by the process of claim 1.

* * * * *